US008642506B2

(12) United States Patent
Sakurai et al.

(10) Patent No.: US 8,642,506 B2
(45) Date of Patent: Feb. 4, 2014

(54) PLANT DISEASE DAMAGE CONTROL COMPOSITION AND PLANT DISEASE DAMAGE PREVENTION AND CONTROL METHOD

(75) Inventors: Seiya Sakurai, Sanbu-gun (JP); Junro Kishi, Chiba (JP); Hideo Kawashima, Morbaara (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 62 days.

(21) Appl. No.: 12/515,878

(22) PCT Filed: Nov. 21, 2007

(86) PCT No.: PCT/JP2007/072528
§ 371 (c)(1),
(2), (4) Date: May 21, 2009

(87) PCT Pub. No.: WO2008/062823
PCT Pub. Date: May 29, 2008

(65) Prior Publication Data
US 2010/0056589 A1 Mar. 4, 2010

(30) Foreign Application Priority Data

Nov. 21, 2006 (JP) ................... 2006-314312
Nov. 29, 2006 (JP) ................... 2006-321406

(51) Int. Cl.
*A01N 43/56* (2006.01)
*A01N 43/80* (2006.01)
*A01N 41/06* (2006.01)
*A01P 3/00* (2006.01)

(52) U.S. Cl.
USPC ............ 504/100; 514/380; 514/406; 514/604

(58) Field of Classification Search
USPC ........................... 514/380, 406, 604; 504/100
See application file for complete search history.

(56) References Cited

U.S. PATENT DOCUMENTS

| | | | |
|---|---|---|---|
| 4,211,785 A | 7/1980 | Nakagawa et al. | |
| 4,918,106 A * | 4/1990 | Yoshimoto et al. | 514/604 |
| 5,532,365 A | 7/1996 | Kodaka et al. | |
| 5,747,518 A * | 5/1998 | Yoshikawa et al. | 514/403 |
| 2005/0009703 A1 | 1/2005 | Wachendorff-Neumann et al. | |
| 2006/0063829 A1 | 3/2006 | Andersch et al. | |
| 2008/0261811 A1 | 10/2008 | Krohn et al. | |
| 2008/0274882 A1 | 11/2008 | Krohn et al. | |
| 2009/0131462 A1* | 5/2009 | Gewehr et al. | 514/274 |
| 2010/0056594 A1 | 3/2010 | Sakurai et al. | |

FOREIGN PATENT DOCUMENTS

| | | |
|---|---|---|
| EP | 1813152 A1 | 8/2007 |
| JP | 61-197553 A | 9/1986 |
| JP | 3-227904 A | 10/1991 |
| JP | 7-179448 A | 7/1995 |
| JP | 8-198710 A | 8/1996 |
| JP | 8-198713 A | 8/1996 |
| JP | 8-245322 A | 9/1996 |
| JP | 8-245323 A | 9/1996 |
| JP | 8-291009 A | 11/1996 |
| JP | 9-235282 A | 9/1997 |
| JP | 11-5708 A | 1/1999 |
| JP | 11-228309 A | 8/1999 |
| JP | 11-292715 A | 10/1999 |
| JP | 11-302107 A | 11/1999 |
| JP | 11-302108 A | 11/1999 |
| JP | 11-302109 A | 11/1999 |
| JP | 11-302110 A | 11/1999 |
| JP | 11-302111 A | 11/1999 |
| JP | 11-322511 A | 11/1999 |
| JP | 2001-72511 A | 3/2001 |
| JP | 2001-72512 A | 3/2001 |
| JP | 2001-72513 A | 3/2001 |
| JP | 2001-81003 A | 3/2001 |
| JP | 2004-538325 A | 12/2004 |
| JP | 2005-517714 A | 6/2005 |
| JP | 2006-213664 A | 8/2006 |
| JP | 2009-501768 A | 1/2009 |
| WO | WO 2005/092100 A1 | 10/2005 |
| WO | WO 2006/036827 A1 | 4/2006 |
| WO | WO 2006/069654 A2 | 7/2006 |
| WO | WO 2006/069655 A1 | 7/2006 |
| WO | WO 2006/082723 A1 | 8/2006 |
| WO | WO 2006/094978 | 9/2006 |
| WO | WO 2006/105888 A2 | 10/2006 |
| WO | WO 2007/010036 A2 | 1/2007 |
| WO | WO 2007/039214 A1 | 4/2007 |

(Continued)

OTHER PUBLICATIONS

Farm Chemicals Handbook '98, Meister Publishing Co., Willoughby (Ohio), p. C216 (1998).*

(Continued)

*Primary Examiner* — John Pak
(74) *Attorney, Agent, or Firm* — Buchanan Ingersoll & Rooney PC

(57) ABSTRACT

The invention provides a plant disease control composition including active ingredients of (RS)-N-[2-(1,3-dimethylbutyl)thiophene-3-yl]-1-methyl-3-trifluoromethyl-1H-pyrazole-4-carboxamide (common name: penthiopyrad) and at least one fungicidal compound other than penthiopyrad, and a plant disease prevention method wherein such a compound is applied to plant seeds or soil. According to the invention, a composition and a prevention method are provided which demonstrate a prevention effect against plural types of disease pathogenic microbes, and also demonstrate a preventing effect to currently emerging resistant pathogenic microbes, when applied to plant seed or soil.

9 Claims, No Drawings

(56) References Cited

FOREIGN PATENT DOCUMENTS

| WO | WO 2007/085565 A1 | 8/2007 |
|---|---|---|
| WO | WO 2008/003738 | 1/2008 |
| WO | WO 2008/062821 A1 | 5/2008 |
| WO | WO 2008/065960 A1 | 6/2008 |

OTHER PUBLICATIONS

International Search Report (PCT/ISA/210) dated Dec. 12, 2007.
Written Opinion (PCT/ISA/237) dated Dec. 12, 2007.
U.S. Appl. No. 12/516,966, filed May 29, 2009, Yamada et al.
Translation of JP 2006-213664 (Aug. 2006).
Webster's New World Dictionary, 2nd college ed., The World Publishing Co., NY, entry for "prevent," p. 1127 (1972).
Derwent abstract 2006-573208; abstracting JP 2006-213664 (Aug. 2006).
Machine translation of JP 2006-213664 (Aug. 2006).
International Search Report (PCT/ISA/210) dated Jan. 8, 2008.
Written Opinion (PCT/ISA/237) dated Jan. 8, 2008.
Office Action issued in the corresponding Australian Patent Application No. 2007322691 dated Apr. 14, 2010.
Office Action issued in corresponding Russian Patent Application No. 2009122652/15 (031298) dated Feb. 12, 2010, and an English Translation thereof.
Notice of Reasons for Rejection issued in corresponding Japanese Patent Application No. 2008-545427 dated Mar. 21, 2012.
Office Action issued in corresponding Columbian Patent Application No. 09 064 115 dated Jul. 27, 2012 with English translation.
Chilean Office Action dated Nov. 20, 2012, issued in corresponding Chilean patent application.
Extended European Search Report issued in corresponding EP 07 83 2258 dated Sep. 25, 2012.

* cited by examiner

PLANT DISEASE DAMAGE CONTROL COMPOSITION AND PLANT DISEASE DAMAGE PREVENTION AND CONTROL METHOD

FIELD OF THE INVENTION

The invention relates to a plant disease damage control composition and to a plant disease damage prevention and control method.

BACKGROUND OF THE INVENTION

It is described in Japanese Patent Application Laid-Open (JP-A) No. 9-235282 that penthiopyrad shows an effect as a fungicidal compound in application methods such as seed sterilization, foliar spray application, and the like, against: rice diseases of rice blast disease (*Pyricularia oryzae*), brown spot (*Cochliobolus miyabeanus*), sheath blight disease (*Rhizoctonia solani*) and bakanae disease (*Gibberella fujikuroi*); wheat-like cereal diseases such as powdery mildew (*Erysiphe graminis*), barley stripe (*Pyrenophora graminea*), *Typhula* snow mold (*Typhula* sp.) and loose smut (*Ustilago tritici*); powdery mildew of grapes (*Uncinula necator*); powdery mildew of apples (*Podosphaera leucotricha*); powdery mildew of cucurbitaceae (*Sphaerotheca fuliginea*); and the like.

Moreover, it is described in JP-A Nos. 11-228309, 11-292715, 11-302107, 11-302108, 11-302109, 11-302110, 11-302111, 2001-072511, 2001-072512, and 2001-072513 that a composition containing penthiopyrad and other fungicidal compound(s) shows an effect, by application method, such as seed sterilization, foliar application, soil application and water application, against: rice diseases of rice blast disease (*Pyricularia oryzae*), brown spot (*Cochliobolus miyabeanus*), sheath blight disease (*Rhizoctonia solani*) and bakanae disease (*Gibberella fujikuroi*); wheat-like cereal diseases of powdery mildew (*Erysiphe graminis*), barley stripe (*Pyrenophora graminea*), *Typhula* snow mold (*Typhula* sp.) and loose smut (*Ustilago tritici*); powdery mildew of grapes (*Uncinula necator*); powdery mildew of apples (*Podosphaera leucotricha*); powdery mildew of cucurbitaceae (*Sphaerotheca fuliginea*); and the like.

However, a control effect is not yet known from mixing penthiopyrad with fenoxanil, trifloxystrobin, tecloftalam, oxytetracycline, streptomycin, mildiomycin, ipconazole, pefurazoate, etridiazole, triticonazole, cyproconazole, copper, basic copper chloride, basic copper sulphate, oxine copper, anhydrous copper sulfate, copper II hydroxide, fuberidazole, tolclofos-methyl, dinocap, thiuram, propineb, zineb, ziram, ambam, hydroxyisoxazol (hymexazol), methasulfocarb, chloropicrin, flusulfamide, dazomet, methylisothiocyanate, potassium salt of hydroxyisoxazol, 1,3-dichloropropene, carbam, rapeseed oil, machine oil, lime sulfur mixture, zinc sulfate, fentin, sodium hydrogencarbonate, potassium hydrogencarbonate, hypochlorite, flumorph, metallic silver, chloroneb, dichlofluanid, dichloram, dithianon, diflumetorim, dimethirimol, silthiofam, spiroxamine, thiaziazine (milneb), tolylfluanid, nitrothal-isopropyl, fenitropan, fenpiclonil, fluopicolide, propamocarb, propamocarb hydrochloride, benthiazole, organic nickel, resveratrol, iminoctadine acetate, tiadinil, guazatine, or triazoxide.

DESCRIPTION OF THE INVENTION

Problem to be Solved by the Invention

An object of the invention is to provide a damage control composition and plant disease damage prevention and control method for preventing new plant diseases, the composition including penthiopyrad and one or more other fungicidal compound as active ingredients and having plural disease damage spectra against pathogenic microbes of various plants, showing an effect also against emerging resistant pathogenic microbes, and furthermore not generating phytotoxicity.

Means for Solving the Problem

As a result of carrying out diligent examination and investigation, the present inventors have determined that a composition that includes penthiopyrad, to which is added one or more other fungicidal compound, demonstrates a high preventative effect in small amounts against damage from plural diseases, and shows a stable prevention effect also to the above resistant pathogenic microbes, without generating phytotoxicity, thereby resulting in the invention.

The means of solving the above problem are as follows.

1. A plant disease control composition comprising active ingredients of:

(RS)-N-[2-(1,3-dimethylbutyl) thiophene-3-yl]-1-methyl-3-trifluoromethyl-1H-pyrazole-4-carboxamide (common name: penthiopyrad); and at least one fungicidal compound other than penthiopyrad selected from the group consisting of hydroxyisoxazol and flusulfamide.

2. The plant disease control composition of claim 1, wherein the at least one fungicidal compound other than penthiopyrad comprises hydroxyisoxazol.

3. The plant disease control composition of claim 1, wherein the at least one fungicidal compound other than penthiopyrad comprises flusulfamide.

4. A plant disease control method demonstrating a control effect to a plant disease, the control method comprising applying the composition of claim 1 to an environment in which a plant disease pathogenic microbe lives.

5. A plant disease control method demonstrating a control effect to a plant disease, the control method comprising applying the composition of claim 1 by: foliar application to plant individuals; spray treatment to the soil surface; soil incorporation after spray treatment to the soil surface; injection treatment into the soil; soil incorporation after injection treatment into the soil; soil drenching treatment; soil incorporation after soil drenching; spray treatment of plant seeds; coating treatment of plant seeds; dip treatment of plant seeds; or dressing treatment of plant seeds.

6. A plant disease control method demonstrating a control effect to a plant disease, the control method comprising applying the composition of claim 3 to an environment in which a plant disease pathogenic microbe lives, by: spray treatment to the soil surface; soil incorporation after spray treatment to the soil surface; injection treatment into the soil; soil incorporation after injection treatment into the soil; or soil incorporation after soil drenching.

7. An agricultural formulation comprising the composition according to claim 1 selected from the group consisting of a wettable powder, a flowable, a granular wettable powder, a powder formulation, and an emulsion.

Effect of the Invention

According to the plant disease damage control composition and plant disease damage control method of the invention, a high preventive effect to disease damage generated in plants is demonstrated, and also a stable preventive effect is shown to existing chemically resistant pathogenic microbes, and phytotoxicity is not discerned.

BEST MODE OF CARRYING OUT THE INVENTION

Specific examples of the types of disease damage which may be prevented with the plant disease damage control composition and the plant disease damage control method of the invention include, but are not limited to, the following:

rice diseases such as rice blast disease (*Pyricularia oryzae*), sheath blight disease (*Rhizoctonia solani*), brown spot (*Cochliobolus miyabeanus*), bakanae disease (*Gibberella fujikuroi*), seedling damping off (*Fusarium roseum, Fusarium solani, Pythium monospermum, Pythium diclinum, Pythium aphanidermatum*);

wheat-like cereal diseases such as powdery mildew (*Erysiphe graminis* f. sp. hordei; f. sp. tritici), rust (*Puccinia striiformis, Puccinia graminis, Puccinia recondita, Puccinia hordei*), barley stripe (*Pyrenophora graminea*), net blotch (*Pyrenophora teres*), fusarium head blight (*Fusarium graminearum, Fusarium culmorum, Fusarium avenaceum, Microdochium nivale*), Typhula snow mold (*Typhula* sp., *Micronectriella nivalis*), loose smut (*Ustilago nuda, Ustilago tritici, Ustilago nigra, Ustilago avenae*), bunts (*Tilletia caries, Tilletia pancicii*), eyespot (*Pseudocercosporella herpotrichoides*), foot rot (*Rhizoctonia cerealis*), scald (*Rhynchosporium secalis*), leaf blotch (*Septoria tritici*), glume blotch (*Leptosphaeria nodorum*);

grape diseases such as downy mildew (*Plasmopora viticola*), rust (*Phakopsora ampelopsidis*), powdery mildew (*Uncinula necator*), anthracnose (*Elsinoe ampelina*) and ripe rot (*Glomerella cingulata*);

apple diseases such as powdery mildew (*Podosphaera leucotricha*), apple scab (*Venturia inaequalis*), *Alternaria* blotch (*Alternaria mali*), apple rust (*Gymnosporangium yamadae*), moniliasis (*Sclerotinia mali*) and valsa canker (*Valsa mali*);

pear diseases such as black spot (*Alternaria kikuchiana*), pear scab (*Venturia nashicola*), pear rust (*Gymnosporangium haraeanum*) and *Physalospora* canker (*Physalospora piricola*);

peach diseases such as brown rot (*Sclerotinia cinerea*), scab (*Cladosporium carpophilum*) and *Phomopsis* rot (*Phomopsis* sp.);

persimmon diseases such as anthracnose (*Gloeosporium kaki*), leaf spot (*Cercospora kaki; Mycosphaerella nawae*) and powdery mildew (*Phyllactinia kakikora*);

gray mould (*Botrytis cinerea*) of kidney bean, cucumber, tomato, strawberry, grape, potato, soybeans, cabbage, eggplant, lettuce and the like;

seedling blight (*Rhizoctonia solani, Pythium vexans, Pythium cucurbitaccarum, Pythium debaryanum, Pythium hemmianum*) of various vegetables, such as tomato, cucumber, Japanese radish, watermelon, eggplant, sweet pepper, spinach and the like;

downy mildew of cucumber (*Pseudoperonospora cubensis*);

cucurbitaceae diseases such as powdery mildew (*Sphaerotheca fuliginea*), anthracnose (*Colletotrichum lagenarium*), gummy stem blight (*Mycosphaerella melonis*) and cucurbitaceae *Fusarium* wilt (*Fusarium oxysporum*);

tomato diseases such as early blight (*Alternaria solani*), leaf mould (*Cladosporium falvum*), late blight (*Phytophthora infestans*), tomato wilt (*Fusarium oxysporum*);

eggplant diseases such as powdery mildew (*Erysiphe cichoracearum*), leaf mould (*Mycovellosiella nattrassii*);

Brassicaceae vegetable diseases such as *Alternaria* leaf spot (*Alternaria brassicae*), white spot (*Cercosporella brassicae*), black leg (*Leptospheria maculans*), club root (*plasmodiophora brassicae*);

cabbage diseases such as foot rot (*Rhizoctonia solani*), *Sclerotinia* rot (*Sclerothinia sclerotorium*), cabbage yellows (*Fusarium oxysporum*);

chinese cabbage diseases such as bottom rot (*Rhizoctonia solani*), chinese cabbage yellows (*Verticillium dahliae*);

leek diseases such as rust (*Puccinia allii*), *Alternaria* leaf spot (*Alternaria porri*), southern blight (*Sclerotium rolfsii*);

legume diseases such as seedling blight (*Rhizoctionia solani*) and *Sclerotinia* stem rot (*Sclerothinia sclerotorium*);

soya bean diseases such as purple seed stain (*Cercospora kikuchii*), Anthracnose (*Elsinoe glycinnes*), stem canker (*Diaporthe phaseolorum*) and *Rhizoctonia* root rot (*Rhizoctonia solani*);

kidney bean diseases such as anthracnose (*Colletotrichum lindemuthianum*; peanut diseases such as black leaf spot (*Mycosphaerella personatum*), brown leaf spot (*Cercospora arachidicola*);

pea diseases such as powdery mildew (*Erysiphe pisi*) and downy mildew (*Peronospora pisi*);

potato diseases such as early blight (*Alternaria solani*), black scarf (*Rhizoctonia solani*), late blight (*Phytophthora infestans*);

broad bean diseases such as downy mildew (*Peronospora viciae*) and *Phytophthora* rot (*Phytophthora nicotianae*);

tea diseases such as net blister blight (*Exobasidium reticulatum*), white scab (*Elsinoe leucospila*), anthracnose (*Colletotrichum theaesinensis*);

tobacco diseases such as brown spot (*Alternaria longipes*), powdery mildew (*Erysiphe cichoracearum*), anthracnose (*Colletotrichum tabacum*) and black shank (*Phytophthora parasitica*);

sugar beet diseases such as *cercospora* leaf spot (*Cercospora beticola*);

rose diseases such as black spot (*Diplocarpon rosae*), powdery mildew (*Sphaerotheca pannosa*) and *Phytophthora* Rot (*Phytophthora megasperma*);

chrysanthemum diseases such as brown leaf spot (*Septoria chrysanthemiindici*) and white rust (*Puccinia horiana*);

strawberry diseases such as powdery mildew (*Sphaerotheca humuli*) and *Phytophthora* Rot (*Phytophthora nicotianae*);

*Sclerotinia* stem rot (*Sclerotinia sclerotiorum*) of kidney bean, cucumber, tomato, strawberry, grape, potato, soybeans, cabbage, eggplant, lettuce, and the like;

melanose (*Diaporthe citri*) of citrus;

leaf blight (*Alternaria dauci*) of carrot; and the like.

The composition of the invention may be used as it is, however, the composition of the invention is usually used by mixing with a carrier and formulating by generally known methods, into a wettable powder, a flowable, a granular wettable powder, a powder formulation, an emulsion, and the like, with the addition of adjuvant(s) for formulation, such as surfactants, wetting agents, sticking agents, thickeners, preservatives, colorants, and/or stabilizers, as the need arises. The content of the penthiopyrad active ingredient in such formulations is usually in the range of from 0.005% to 99% by weight, preferably 0.01% to 90% by weight, and still more preferably 0.1% to 85% with respect to the total amount of the formulation. On the other hand, the content of the fungicide(s) other than penthiopyrad are usually in the range of from 0.005% to 99% by weight, and preferably from 0.1% to 70% by weight with respect to the total amount of the formulation. The total amount of the penthiopyrad and the other fungicide(s) is usually in the range of 0.005% to 99% by weight, preferably from 0.01% to 90% by weight, and still more preferably from 0.1% to 85% with respect to the total amount of the formulation.

A carrier used for the above composition refers to a synthetic or natural, organic or inorganic, substance that assists delivery of the active ingredients to the site requiring treatment, or a substance blended with the active ingredient compounds in order to facilitate storing, delivery and handling thereof. Such a carrier is not particularly limited, and if it is a carrier that is usually used for horticultural chemicals then either a solid or a liquid carrier may be used. As a solid carrier, the following may be given as examples: inorganic substances, such as bentonite, montmorillonite, kaolinite, diatomaceous earth, white clay, talc, clay, vermiculite, gypsum, calcium carbonate, amorphous silica and ammonium sulfate; vegetable organic substances, such as soya bean flour, wood flour, saw dust, wheat flour, lactose, sucrose, and glucose; and urea and the like. As a liquid carrier, the following may be given as examples: aromatic hydrocarbons such as toluene, xylene and cumene, and naphthenes; paraffin hydrocarbons, such as n-paraffin, iso-paraffin, liquid paraffin, kerosene, mineral oil and polybutene; ketones, such as acetone and methyl ethyl ketone; ethers, such as dioxane and diethylene glycol dimethyl ether; alcohols, such as ethanol, propanol, and ethylene glycol; carbonates, such as ethylene carbonate, propylene carbonate, and butylene carbonate; aprotic solvents such as dimethylformamide, and dimethyl sulfoxide; and water, and the like.

Furthermore, the following adjuvants may also be used, according to the purpose and in consideration of the form of the formulation, the treatment method and the like, in order to reinforce the effect of the invention compounds, and these adjuvants may be used singly or in combinations thereof.

As adjuvants, surfactants may be used that are usually used in agricultural formulation for purposes such as emulsification, dispersion, spreading, and wetting, and examples that may be given of such surfactants include, but are not limited to: nonionic surfactants such as sorbitan fatty acid esters, polyoxyethylene sorbitan fatty acid esters, sucrose fatty acid esters, polyoxyethylene fatty acid esters, polyoxyethylene resin acid esters, polyoxyethylene fatty acid diesters, polyoxyethylene castor oils, polyoxyethylene alkyl ethers, polyoxyethylene alkyl phenyl ethers, polyoxyethylene dialkyl phenyl ethers, formaldehyde condensates of polyoxyethylene alkyl phenyl ethers, polyoxyethylene-polyoxypropylene block polymers, alkyl polyoxyethylene-polyoxypropylene block polymer ethers, alkylphenyl polyoxyethylene-polyoxypropylene block polymer ethers, polyoxyethylene alkylamines, polyoxyethylene fatty acid amides, polyoxyethylene bisphenyl ethers, polyoxyalkylene benzylphenyl ethers, polyoxyalkylene styryl phenyl ethers, polyoxyalkylene adducts of a higher alcohol, polyoxyethylene ethers, ester modified silicones, and fluorosurfactants; anionic surfactants such as alkyl sulfates, polyoxyethylene alkyl ether sulfates, polyoxyethylene alkylphenyl ether sulfates, polyoxyethylene benzylphenyl ether sulfates, polyoxyethylene styryl phenyl ether sulfates, polyoxyethylene-polyoxypropylene block polymer sulfates, paraffin sulfonates, alkane sulfonates, AOS, dialkyl sulfosuccinate, alkylbenzene sulfonates, naphthalene sulfonates, dialkyl naphthalene sulfonates, formaldehyde condensates of naphthalene sulfonates, alkyl diphenyl ether disulfonates, lignin sulfonates, polyoxyethylene alkyl phenyl ether sulfonates, polyoxyethylene alkyl ether sulfosuccinate half esters, fatty acid salts, N-methyl fatty acid sarcosinate, resinates, polyoxyethylene alkyl ether phosphates, polyoxyethylene phenyl ether phosphates, polyoxyethylene dialkyl phenyl ether phosphates, polyoxyethylene benzylated phenyl ether phosphates, polyoxyethylene benzylated phenylphenyl ether phosphates, polyoxyethylene styrylated phenyl ether phosphates, polyoxyethylene styrylated phenylphenyl ether phosphates, polyoxyethylene-polyoxypropylene block polymer phosphates, polyoxyethylene diallyl ether sulfates, phosphatidylcholine, phosphatidyl ethanolimine, alkyl phosphates and sodium tripolyphosphates; polyanion type high molecular surfactants derived from acrylic acid with acrylonitrile, acrylamide methylpropanesulfonic acid; cationic surfactants, such as alkyl trimethyl ammonium chlorides, methyl polyoxyethylene alkyl ammonium chlorides, alkyl N-methylpyridinium bromides, mono-methylated ammonium chloride, dialkyl methylated ammonium chlorides, alkyl pentamethyl propylene amine dichlorides, alkyl dimethyl benzalkonium chlorides, and benzethonium chloride; and amphoteric surfactants, such as dialkyl diaminoethyl betaines and alkyl dimethyl benzyl betaines.

As a binder, examples that may be given include sodium arginate, polyvinyl alcohol, gum arabic, sodium CMC, bentonite, and the like.

Examples that may be given of disintegrants include sodium CMC, crosscarmellose sodium, and examples of stabilizers include hindered phenol antioxidants, benzotriazol based and hindered amine based ultraviolet absorbers, and the like.

Phosphoric acid, acetic acid, and sodium hydroxide may be used as a pH adjuster, and industrial fungicides and antifungal agents, such as 1,2-benzisothiazolin-3-one and the like, may be added for prevention of bacteria and molds.

As a thickener, xanthane gum, guar gum, sodium CMC, gum arabic, polyvinyl alcohols, montmorillonite, and the like may also be used.

As required, silicone compounds may be used as antifoaming agents, and propylene glycol, ethylene glycol, and the like may be used as antifreezing agents.

Examples that may be given of application methods for the composition of the invention include foliar application to plant individuals, spray treatment to the soil surface, soil incorporation after spray treatment to the soil surface, soil injection treatment, and soil incorporation after soil injection treatment, soil drenching, and soil incorporation after soil drenching treatment, spray treatment to plant seeds, coating treatment to plant seeds, dip treatment to plant seeds, dressing treatment to plant seeds and the like, but sufficient effect may be demonstrated by any application method commonly used by a person skilled in the art. The amount of application and the application concentration vary according to the type of crop and disease damage to be targeted, the level of incidence of the disease, the formulation type of the compound, the application method, various environmental conditions, and the like, however, the amount of active ingredients is suitably from 50 g to 10,000 g per hectare when used in spraying, and is preferably from 100 g to 5,000 g per hectare. When diluting with water and spraying a wettable powder, a flowable, or an emulsion, the dilution rate is suitably from 5 to 50,000 times; preferably from 10 to 20,000 times, and still more preferably from 15 to 10,000 times. In the case of seed sterilization, the amount of the fungicide mixture used may be from 0.001 g to 50 g per kg of seed, and preferably from 0.01 g to 10 g.

When carrying out foliar application to plant individuals, spray treatment to the soil surface, injection treatment into the soil, and soil drenching treatment with the composition of the invention, the chemicals being used may be diluted to a suitable concentration with a suitable carrier. When contacting the composition of the invention to plant seeds, the plant seeds may be immersed in the composition as it is. Alternatively, after diluting the chemicals to be used with a suitable carrier to a suitable concentration, the chemicals may be used by dipping, dressing, spraying, or coating to plant seeds. For carrying out dressing, spraying, and coating treatment, a suitable amount of the formulation used is usually about from 0.05% to 50% of dry plant seed weight, and more preferably from 0.1% to 30%. However, the amount used is not limited to these ranges, and may be varied according to the form of the formulation and to the kind of plant seed used as the candidate for treatment. There are no particular limitations to suitable carriers, and examples that may be given thereof include: liquid carriers, such as water or organic solvents such as ethanol; and include solid carriers, such as inorganic substances like bentonite, montmorillonite, kaolinite, diatomaceous earth, white clay, talc, clay, vermiculite, gypsum, calcium carbonate, amorphous silica, and ammonium sulfate; vegetable organic substances, such as soya bean flour, wood flour, saw dust, wheat flour, lactose, sucrose, and glucose; and urea.

The plant individuals referred to in the invention are living organisms that carry out photosynthesis but do not move. Specific examples that may be given thereof include, but are not limited to: corn, soybean, cotton, rice, sugar beet, wheat, barley, sunflower, tomato, cucumber, eggplant, spinach, podded peas, Japanese pumpkin, sugarcane, tobacco, sweet pepper, sweet potato, taro, konnyaku, sugar beet, grape, apple, pear, peach, tulip, and chrysanthemum.

In the invention, plant seed refers to something that stores nutrients for seedlings to sprout and is used for propagation in agriculture. Specific examples that may be given include: seeds, such as corn, soya bean, cotton, rice, sugar beet, wheat, barley, sunflower, tomato, cucumber, eggplant, spinach, podded peas, Japanese pumpkin, sugarcane, tobacco, sweet pepper, and rape; seed potatoes, such as taro, potato, sweet potato, and konnyaku; bulbs, such as edible lily and tulip; and seed bulbs, such as shallot. Further examples that may be given are plants that do not initially exist in nature but are produced by manipulating genes and the like artificially, thereby undergoing genetic transformation, such as, but not limited to: herbicide-tolerant soya bean, corn, cotton and the like; cold adapted rice, tobacco and the like; and corn, cotton, potato and the like imparted with the functionality of producing insecticidal substances.

The composition of the invention may, of course, be mixed with agricultural chemicals, such as other fungicides, pesticides, acaricides, nematocides, herbicides, and plant growth regulators, soil conditioners, and substances with a fertilizing effect.

Examples of fungicides that may be given, without limitation thereto, include: azole fungicides like triadimefon, hexaconazole, prochloraz and triflumizole; acylalanine fungicides like metalaxyl and oxadixyl; benzimidazole fungicides like thiophanate-methyl and benomyl; dithiocarbamate fungicides like mancozeb; tetrachloroisophthalonitrile; and sulfur. Examples of pesticides that may be given, without limitation thereto, include: phosphorus based pesticides like fenitrothion, diazinon, pyridaphenthion, chlorpyrifos, malathion, phenthoate, dimethoate, disulfoton, prothiofos, DDVP, acephate, salithion and EPN; carbamate pesticides like NAC, MTMC, BPMC, pirimicarb, carbosulfan and methomyl; pyrethroid pesticides like etofenprox, silafluofen, permethrin, and fenvalerate; and neonicotinoid insecticides like dinotefuran, clothianidin, nitenpyram, thiamethoxam, imidacloprid, thiacloprid and acetamiprid; fipronil and ethiprole.

EXAMPLES

The invention will now be explained in detail, with reference to Examples and Test Examples.

Example 1

Powder Formulation 5 parts of penthiopyrad, 4 parts of hydroxyisoxazol, 90.5 parts of clay, and 0.5 parts of DRILESS B (trade name, an aggregating agent made by Sankyo Co., Ltd.) were uniformly mixed together and ground, and a powder formulation containing 5% of the active ingredient of penthiopyrad and 4% of the active ingredient of hydroxyisoxazol was obtained.

Reference Example 1

Powder Formulation 5 parts of penthiopyrad, 94.5 parts of clay, and 0.5 parts of DRILESS B (trade name, an aggregating agent made by Sankyo Co., Ltd.) were uniformly mixed together and ground, and a powder formulation containing 5% of the active ingredient of penthiopyrad was obtained.

Example 2

Wettable Powder 25 parts of penthiopyrad, 4 parts of flusulfamide, 1 part of sodium ligninsulfonate, 5 parts of amorphous silica, and 65 parts of diatomaceous earth were mixed together and ground, and a wettable powder containing 25% of the active ingredient of penthiopyrad and 4% of the active ingredient of flusulfamide was obtained.

Reference Example 2

Wettable Powder 25 parts of penthiopyrad, 1 part of sodium ligninsulfonate, 5 parts of amorphous silica, and 69 parts of diatomaceous earth were mixed together and ground, and a wettable powder containing 25% of the active ingredient of penthiopyrad was obtained.

Reference Example 3

Wettable Powder 4 parts of flusulfamide, 1 part of sodium ligninsulfonate, 5 parts of amorphous silica, and 90 parts of diatomaceous earth were mixed together and ground, and a wettable powder containing 4% of the active ingredient of flusulfamide was obtained.

Example 3

Powder Formulation 30 parts of penthiopyrad, 35 parts of hydroxyisoxazol and 34.5 parts of clay, and 0.5 parts of DRILESS B (trade name, an aggregating agent made by Sankyo Co., Ltd.) were uniformly mixed together and ground, and a powder formulation containing 30% of the active ingredient of penthiopyrad and 35% of the active ingredient of hydroxyisoxazol was obtained.

Reference Example 4

Powder Formulation 30 parts of penthiopyrad and 69.5 parts of clay, and 0.5 parts of DRILESS B (trade name, an aggregating agent made by Sankyo Co., Ltd.) were uniformly mixed together and ground, and a powder formulation containing 30% of the active ingredient of penthiopyrad was obtained.

Reference Example 5

Powder Formulation 35 parts of hydroxyisoxazol and 64.5 parts of clay, and 0.5 parts of DRILESS B (trade name, an aggregating agent made by Sankyo Co., Ltd.) were uniformly mixed together and ground, and a powder formulation containing 35% of the active ingredient of hydroxyisoxazol was obtained.

Example 4

Powder Formulation 1 part of penthiopyrad, 0.3 parts of flusulfamide, 98.2 parts of clay, and 0.5 parts of DRILESS B (trade name, an aggregating agent made by Sankyo Co., Ltd.) were uniformly mixed together and ground, and a powder formulation containing 1% of the active ingredient of penthiopyrad and 0.3% of the active ingredient of flusulfamide was obtained.

Reference Example 6

Powder Formulation 1 part of penthiopyrad and 98.5 parts of clay, and 0.5 parts of DRILESS B (trade name, an aggregating agent made by Sankyo Co., Ltd.) were uniformly mixed together and ground, and a powder formulation containing 1% of the active ingredient of penthiopyrad was obtained.

Test Example 1

Control Effect Against Sugar Beet Seedling Damping Off

A *Rhizoctonia* culture and a *Pythium* culture were separately cultivated at 25° C. for seven days in a wheat bran medium, and after respectively grinding, the *Rhizoctonia* culture and/or the *Pythium* culture were added to and mixed in with sterilized soil, at amounts of:

0.1% of *Rhizoctonia* culture with respect to the weight of sterilized soil;

0.1% of *Pythium* culture with respect to the weight of sterilized soil; and 0.1% of *Rhizoctonia* culture and 0.1% of Physium culture with respect to the weight of sterilized soil. These were filled in plastic pots and the infected soils were thus obtained.

Subsequently, amounts of 17.5% and 8.75% with respect to the weight of the seeds of each of the respective powder formulations of Example 1 and Reference Example 1 (comparative chemical), and amounts of 0.5% and 1.0% with respect to the weight of the seeds of a commercially available seed fungicide (TACHIGAREN, trade name, a dust coating agent containing hydroxyisoxazol, made by Sankyo Agro Co., Ltd.) were respectively added to sugar beet seeds (variety: ABEND), and mixed. Sowing was carried out at five seeds per pot, with a total of 20 pots, respectively, of the sugar beet seed to which chemical treatment had been carried out and the sugar beet seed to which no chemical treatment had been carried, and grown on in a greenhouse. The number of non-sprouting seeds at 7 days after sowing, and the seedling dieback number at 14 days after sowing were examined with the naked eye, and the seedling dieback rate was computed by the following Formula 1. Moreover, the existence or not of occurrences of phytotoxicity was also examined with the naked eye. Results are shown in Table 1.

Seedling dieback rate=((number of non-sprouting seeds+seedling dieback number)/number of seeds sown)×100    Formula 1:

TABLE 1

| Test compound | Powder formulation amount (g/ kg seed) | Seedling dieback rate in soil infected by *Rhizoctonia* only (%) | Seedling dieback rate in soil infected by *Pythium* only (%) | Seedling dieback rate in soil infected by *Rhizoctonia* and *Pythium* (%) | Phytotoxicity |
|---|---|---|---|---|---|
| Powder formulation of the invention (Example 1) | 175.0 | 0.7 | 0.9 | 0.7 | None |
| | 87.5 | 2.5 | 3.5 | 1.3 | None |
| Comparative powder formulation (Reference Example 1) | 175.0 | 2.7 | 52.7 | 52.1 | None |
| | 87.5 | 3.3 | 51.3 | 50.6 | None |
| Control seed disinfectant TACHIGAREN dust coating agent | 10.0 | 65.8 | 1.1 | 59.1 | None |
| | 5.0 | 63.9 | 4.3 | 58.6 | None |
| No treatment | — | 65.3 | 50.4 | 57.5 | |

Test Example 2

Control Effect Against Common Scab and Black Scarf in Potato

A *Rhizoctonia* culture was cultivated in a wheat bran medium at 25° C. for seven days, and this was then added at 0.1% with respect to the weight of steam sterilized soil and mixed in uniformly.

A *Rhizoctonia* culture cultivated by the same procedure was added at 0.1% with respect to the weight of soil extracted from a field infected by common scab and mixed in uniformly.

Soil was extracted from a field infected by common scab. These three soil compositions were placed, respectively, into concrete pots (50 cm length×50 cm width×30 cm depth) and the test soils were thereby obtained.

Next, potato seeds of potato (variety: Baron) were dipped into, respectively, 50 times diluents of the wettable powders produced in Example 2, Reference Example 2, and Reference Example 3 (comparative agents), and of a commercial fungicide (NOTTOBAN, trade name, a wettable powder containing tolclofos-methyl and flusulfamide, made by Sumitomo Chemical Co., Ltd.) as a control chemical. The seed potatoes were air dried and two seed potatoes were buried per pot and grown on. For the non-treated plot, seed potatoes that had not undergone chemical treatment were buried. 110 days after burying the seed potatoes, the newly fanned potatoes were dug up, and the existence of disease onset was examined with the naked eye, and the disease onset potato ratio was computed by the following Formula 2. Moreover, the existence or not of occurrences of phytotoxicity was also examined with the naked eye. Five replicates of the above test were performed, and the average values of the results are shown in Table 2.

Disease onset potato ratio=(number of potatoes with disease onset/total number of potatoes examined)×100     Formula 2:

Test Example 3

Control Effect of Damping-Off in Rice Seedlings

A *Rhizoctonia* culture, a *Fusarium* culture and a *Pythium* culture were separately cultivated at 25° C. for seven days in a wheat bran medium, and after respectively grinding, the *Rhizoctonia* culture, the *Fusarium* culture and/or the *Pythium* culture were added to and mixed in with sterilized soil, at amounts of:

0.1% of *Rhizoctonia* culture with respect to the weight of sterilized soil;

0.1% of *Fusarium* culture with respect to the weight of sterilized soil;

0.1% of *Pythium* culture with respect to the weight of sterilized soil;

0.1% of *Rhizoctonia* culture and 0.1% of *Fusarium* culture with respect to the weight of sterilized soil; and 0.1% of *Rhizoctonia* culture and 0.1% of Physium culture with respect to the weight of sterilized soil. The infected soils were thus obtained.

Subsequently, soils in rice seedling boxes were treated with the powder formulation prepared in Example 1 and Reference Example 1, and a commercially available seed fungicide (TACHIGAREN, trade name, a powder formulation containing hydroxyisoxazol made by Sankyo Agro Co., Ltd.) as a control chemical, respectively, at amounts of 3 g and 6 g per rice seedling box (580 mm length×280 mm width×14 mm depth), and well mixed. After filling the above-mentioned infected soils in the rice seedling box, 100 seeds of force sprouted rice seeds were sown, covered with the infected soils and grown on in a greenhouse. The existence of disease onset was examined for all the seedlings with the naked eye at 30 days after starting cultivation, and the disease onset seedling ratio was computed by the following Formula 3. Moreover, the exist-

TABLE 2

| Test compound | Dilution rate | Disease onset potato ratio in soil infected by black scarf only (%) | Disease onset potato ratio in soil infected by common scab only (%) | Disease onset potato ratio in soil infected by black scarf and common scab (%) | Phytotoxicity |
|---|---|---|---|---|---|
| Wettable powder of the invention (Example 2) | 50 times | 0.5 | 18.2 | 18.3 | None |
| Comparative wettable powder (Reference Example 2) | 50 times | 1.3 | 51.6 | 62.8 | None |
| Comparative wettable powder (Reference Example 3) | 50 times | 28.2 | 25.3 | 26.2 | None |
| Control chemical NOTTOBAN wettable powder | 50 times | 1.3 | 27.2 | 28.3 | None |
| No treatment | | 25.2 | 50.5 | 63.1 | | ence or not of occurrences of phytotoxicity was also examined with the naked eye. Results are shown in Table 3.

Disease onset seedling ratio=(number of diseased seedlings/number of seeds sown)×100        Formula 3:

Ltd.) as a control chemical, were distributed, on the surface of the infected soils at 30 kg per 10 are, respectively, and then incorporated into the soils. After the chemical treatment, 100 seeds of cabbage seed (variety: KINKEI No. 201) were sown,

TABLE 3

| Test compound | Powder formulation amount (g/rice seedling box) | Disease onset seedling ratio in soil infected by Rhizoctonia only (%) | Disease onset seedling ratio in soil infected by Fusarium only (%) | Disease onset seedling ratio in soil infected by Pythium only (%) | Disease onset seedling ratio in soil infected by Rhizoctonia and Fusarium (%) | Disease onset seedling ratio in soil infected by Rhizoctonia and Pythium (%) | Phytotoxicity |
|---|---|---|---|---|---|---|---|
| Powder formulation of the invention (Example 1) | 6.0 | 0.1 | 0.5 | 0.3 | 0.1 | 0.2 | None |
|  | 3.0 | 3.5 | 1.5 | 0.7 | 2.5 | 2.4 | None |
| Comparative powder formulation (Reference Example 1) | 6.0 | 0.5 | 23.3 | 45.3 | 23.3 | 44.9 | None |
|  | 3.0 | 5.0 | 35.1 | 44.0 | 33.0 | 45.3 | None |
| Comparative chemical (TACHIGAREN powder formulation) | 6.0 | 52.3 | 2.2 | 0.5 | 43.1 | 43.6 | None |
|  | 3.0 | 51.0 | 3.1 | 0.9 | 47.0 | 44.1 | None |
| No treatment | — | 55.3 | 45.9 | 45.3 | 48.6 | 49.1 |  |

Test Example 4

Control Effect Against *Sclerotinia* Stem Rot and Foot Rot in Cabbage

Test soils were prepared by:

cultivating a *Rhizoctonia* culture at 25° C. for seven days in a wheat bran medium, adding this at 0.1% by weight to soil, and mixing uniformly to provide the test soil for foot rot; and cultivating Sclerotium on a potato dextrose agar medium, adding this at 0.1% by weight to soil, and mixing uniformly to provide the test soil for *Sclerotinia* stem rot.

Next, the infected soils were put in a concrete pot (5 m length×2 m width×60 cm depth), and the powder formulations prepared in Example 4 and Reference Example 6, and a commercial fungicide (NEBIJIN, trade name, a powder formulation containing flusulfamide made by Sankyo Agro Co., respectively, and these were grow on. The existence of disease onset was examined with the naked eye at 110 days after sowing, and disease onset plant ratio was computed by the following formula 4. Moreover, the existence or not of occurrences of phytotoxicity was also examined with the naked eye. Results are shown in Table 4.

Disease onset plant ratio=(number of plants with disease onset/total number of plants examined)×100        Formula 4:

TABLE 4

| Test compound | Powder formulation amount (kg/10 a) | Disease onset plant ratio in soil infected by Sclerotinia stem rot only (%) | Disease onset plant ratio in soil infected by foot rot only (%) | Disease onset plant ratio in soil infected by Sclerotinia stem rot and foot rot (%) | Phytotoxicity |
|---|---|---|---|---|---|
| Powder formulation of the invention (Example 4) | 30 | 4.2 | 4.1 | 4.3 | None |
| Comparative powder formulation (Reference Example 6) | 30 | 10.3 | 10.6 | 9.8 | None |
| Comparative chemical NEBIJIN powder formulation | 30 | 15.3 | 25.1 | 30.3 | None |
| No treatment |  | 30.9 | 40.7 | 48.1 |  |

The invention claimed is:
1. A plant disease control composition comprising active ingredients of:
(RS)-N-[2-(1,3-dimethylbutyl)thiophene-3-yl]-1-methyl-3-trifluoromethyl-1H-pyrazole-4-carboxamide (penthiopyrad); and at least one fungicidal compound other than penthiopyrad selected from the group consisting of hydroxyisoxazole and flusulfamide,
wherein the total amount of penthiopyrad and the at least one fungicidal compound other than penthiopyrad selected from the group consisting of hydroxyisoxazole and flusulfamide is from 0.005 to 99% with respect to the total amount of the composition.

2. The plant disease control composition of claim 1, wherein the at least one fungicidal compound other than penthiopyrad is hydroxyisoxazole.

3. The plant disease control composition of claim 1, wherein the at least one fungicidal compound other than penthiopyrad is flusulfamide.

4. A plant disease control method demonstrating a control effect to a plant disease, the control method comprising applying the composition of claim 3 to an environment in which a plant disease pathogenic microbe lives, by: spray treatment to the soil surface; soil incorporation after spray treatment to the soil surface; or soil drenching.

5. A plant disease control method demonstrating a control effect to a plant disease, the control method comprising applying the composition of claim 1 to an environment in which a plant disease pathogenic microbe lives.

6. A plant disease control method demonstrating a control effect to a plant disease, the control method comprising applying the composition of claim 1 by: spray treatment of plant seeds; coating treatment of plant seeds; dip treatment of plant seeds; or dressing treatment of plant seeds.

7. An agricultural formulation comprising the composition according to claim 1 selected from the group consisting of a wettable powder, a flowable, a granular wettable powder, a powder formulation, and an emulsion.

8. A plant disease control method demonstrating a control effect to a plant disease, the control method comprising applying a composition comprising active ingredients of:
- (RS)-N-[2-(1,3-dimethylbutyl)thiophene-3-yl]-1-methyl-3-trifluoromethyl-1H-pyrazole-4-carboxamide (penthiopyrad); and hydroxyisoxazole to an environment in which a plant disease pathogenic microbe lives,
- wherein the total amount of penthiopyrad and hydroxyisoxazole is from 0.005 to 99% with respect to the total amount of the composition, and
- wherein the composition is in the form of a wettable powder, an emulsion or a flowable, the composition being diluted with water at a dilution rate of 15 to 10,000 times.

9. A plant disease control method demonstrating a control effect to a plant disease, the control method comprising applying a composition comprising active ingredients of:
- (RS)-N-[2-(1,3-dimethylbutyl)thiophene-3-yl]-1-methyl-3-trifluoromethyl-1H-pyrazole-4-carboxamide (penthiopyrad); and hydroxyisoxazole by spray treatment of plant seeds; coating treatment of plant seeds; dip treatment of plant seeds; or dressing treatment of plant seeds,
- wherein the total amount of penthiopyrad and hydroxyisoxazole is from 0.005 to 99% with respect to the total amount of the composition, and
- wherein the composition is applied to the plant seeds in an amount of from 0.1 to 30% of dry plant seed weight.

* * * * *